US00PP24664P3

(12) United States Plant Patent
Wyles

(10) Patent No.: US PP24,664 P3
(45) Date of Patent: Jul. 22, 2014

(54) APPLE TREE NAMED 'FOXTROT'

(50) Latin Name: ***Malus domestica* Borkh.**
Varietal Denomination: Foxtrot

(71) Applicant: Robert Wyles, Tieton, WA (US)

(72) Inventor: Robert Wyles, Tieton, WA (US)

( * ) Notice: Subject to any disclaimer, the term of this patent is extended or adjusted under 35 U.S.C. 154(b) by 130 days.

(21) Appl. No.: 13/573,507

(22) Filed: Sep. 18, 2012

(65) Prior Publication Data

US 2014/0082778 P1 Mar. 20, 2014

(51) Int. Cl.
*A01H 5/00* (2006.01)

(52) U.S. Cl.
USPC ..... Plt./162

(58) Field of Classification Search
USPC ..... Plt./162
See application file for complete search history.

*Primary Examiner* — Wendy C Haas
(74) *Attorney, Agent, or Firm* — Michelle Bos

(57) ABSTRACT

'Foxtrot' is a 'Gala'-type apple variety. It was first selected for its intense red fruit. It is distinguished from 'Tenroy Gala' and other Gala-type varieties by its large, intense red early-maturing fruit and its exceptional flavor.

6 Drawing Sheets

Latin name: *Malus domestica* Borkh.
Variety denomination: 'Foxtrot'.

BACKGROUND OF THE VARIETY

'Foxtrot' is a new and distinct variety of 'Gala'-type apple tree *Malus domestica* Borkh. The new variety is believed to be a whole-tree mutation of 'Tenroy Gala' (U.S. Plant Pat. No. 4,121), and is characterized by its large, intense red early maturing fruit. 'Foxtrot' was first observed in a commercial orchard planted with 'Tenroy Gala' trees near Quincy, Wash. in 2004. After three seasons of observation, the variety was asexually reproduced by grafting to determine whether the desirable characteristics of fruit size, color and early maturity would carry through to subsequent generations. Wood from the second generation trees was grafted onto 'M26' rootstock and planted in a larger commercial planting in 2009 for further observation. 'Foxtrot' has been observed to remain true to type over successive asexually propagated generations.

BRIEF DESCRIPTION OF THE VARIETY

'Foxtrot' is a 'Gala'-type apple variety. It was first selected for its intense red fruit. It is distinguished from 'Tenroy Gala' and other Gala-type varieties by its large, intense red early-maturing fruit and exceptional flavor.

BRIEF DESCRIPTION OF THE PHOTOGRAPHS

Figure 1:
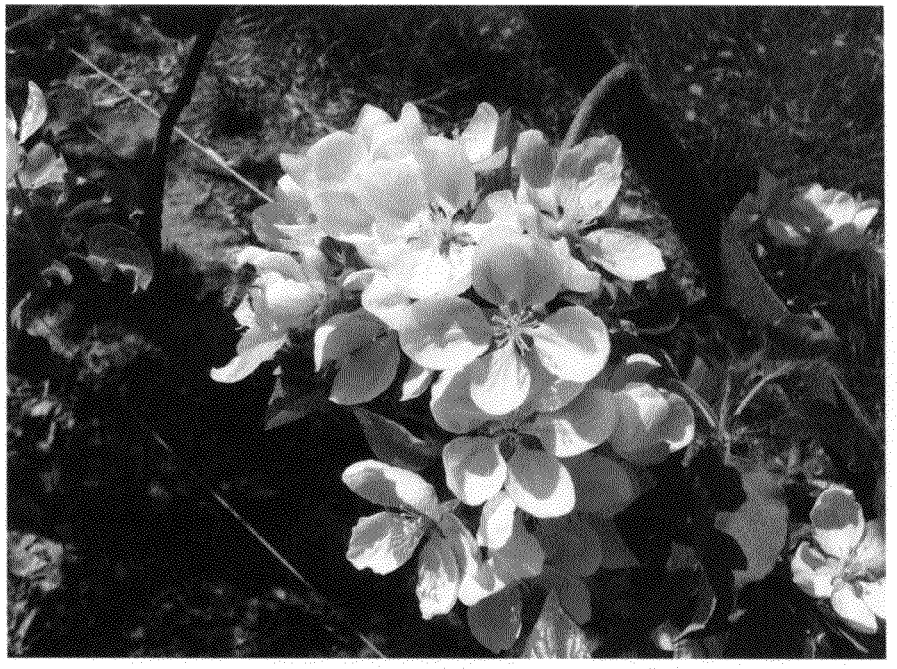
Figure 2:
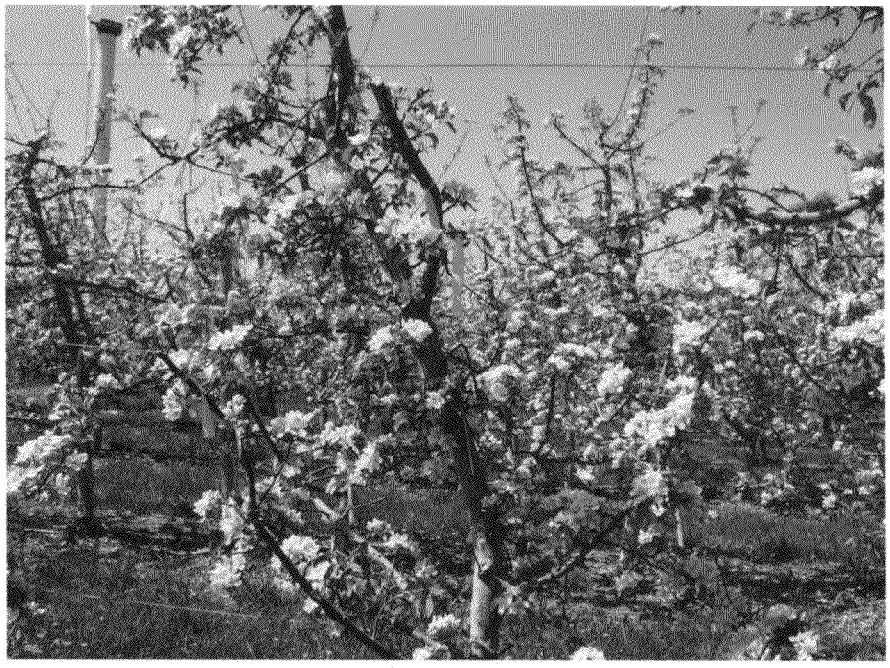
Figure 3:
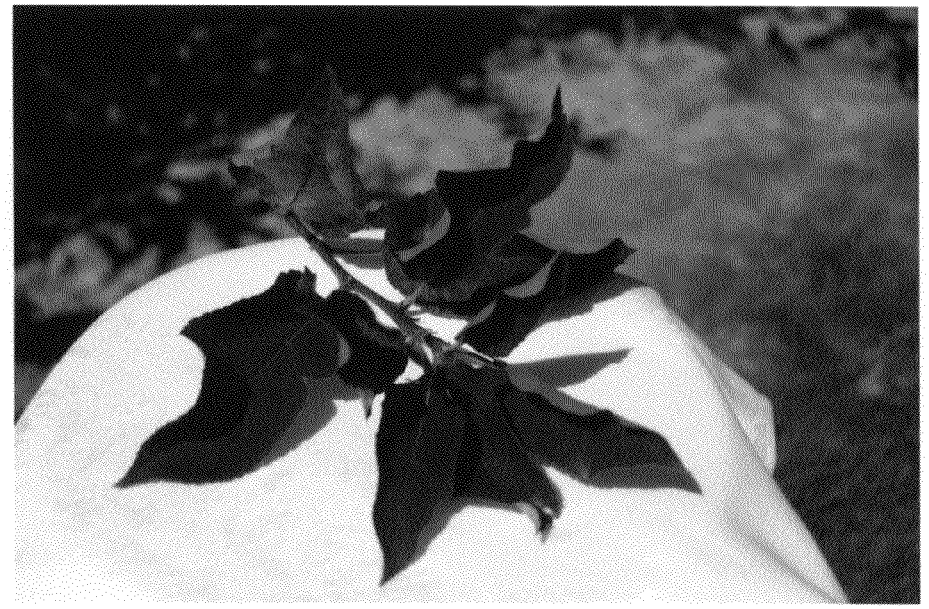
Figure 4:
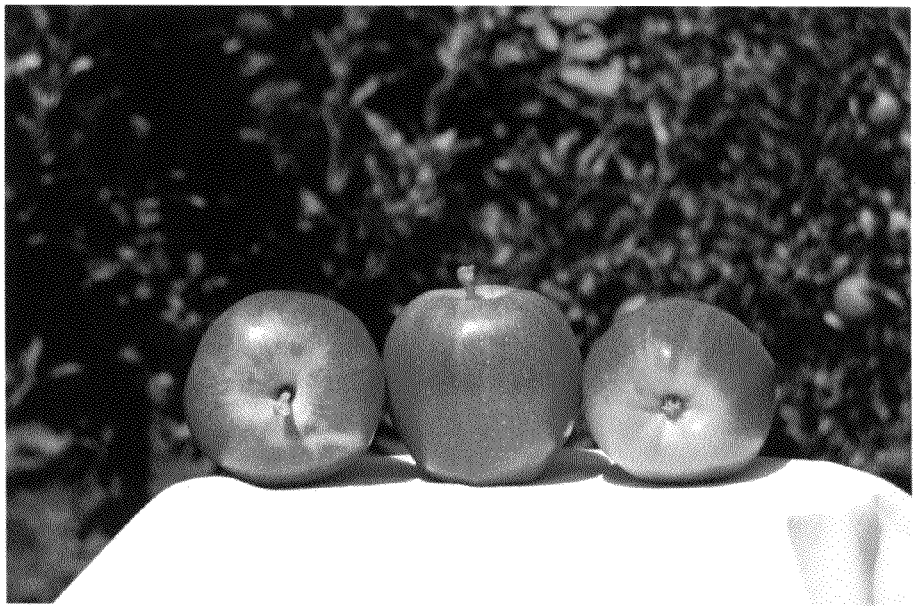
Figure 5:
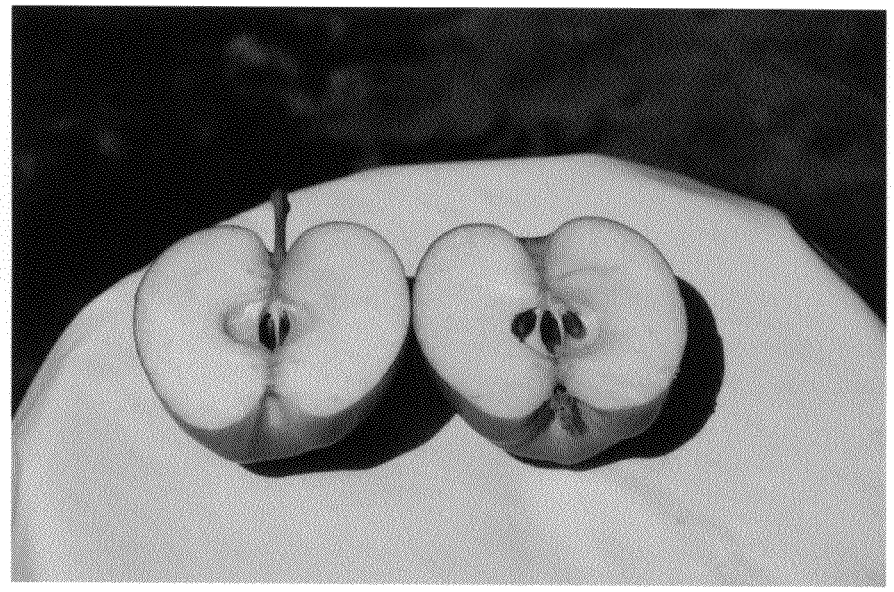
Figure 6:
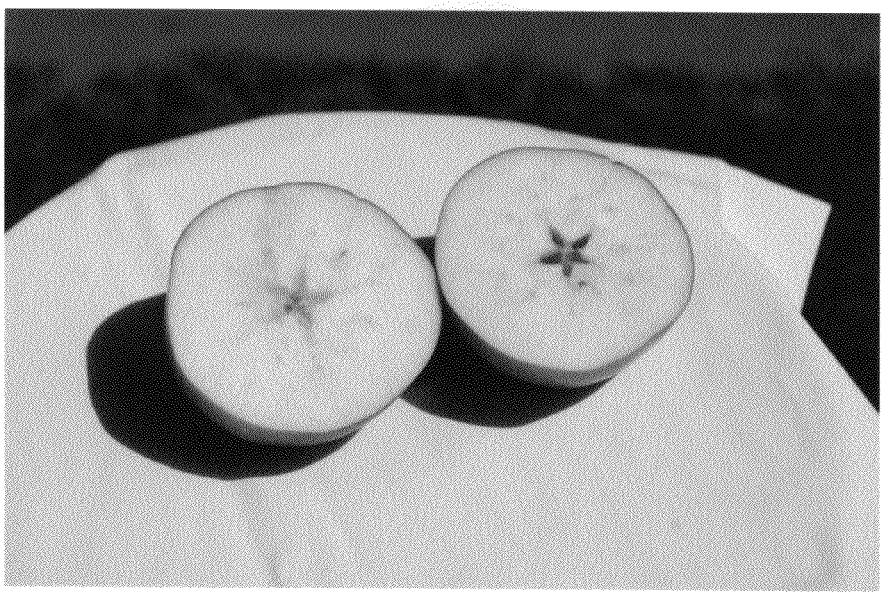
Figure 7:
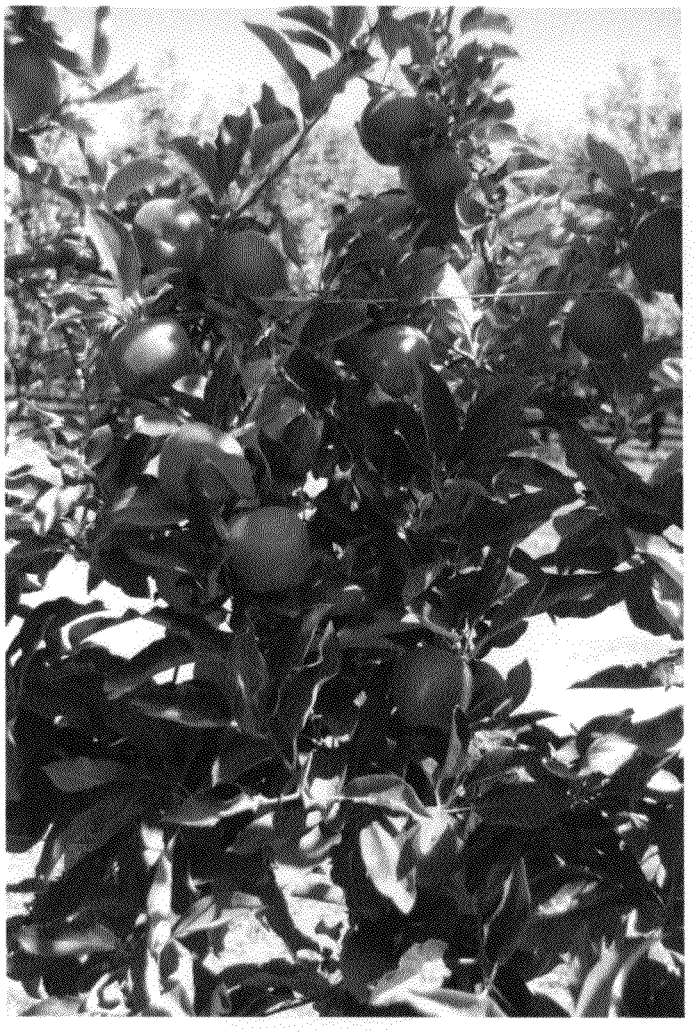
Figure 8:
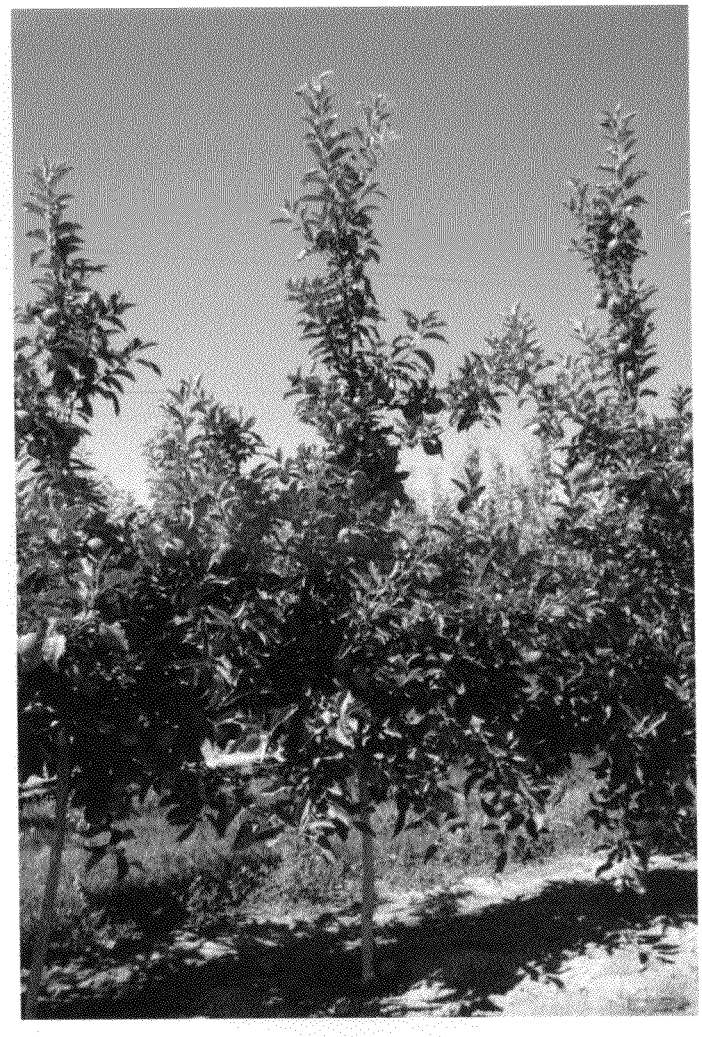
Figure 9:
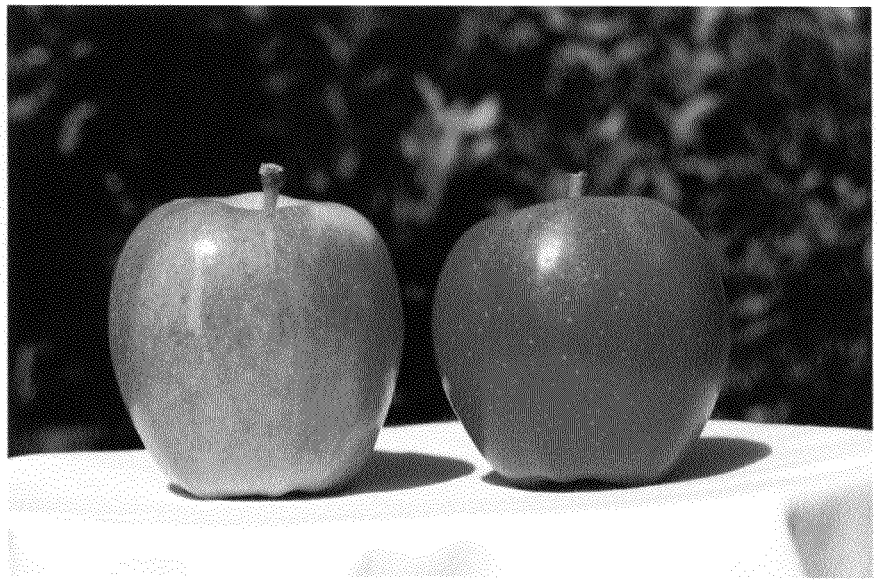
Figure 10:
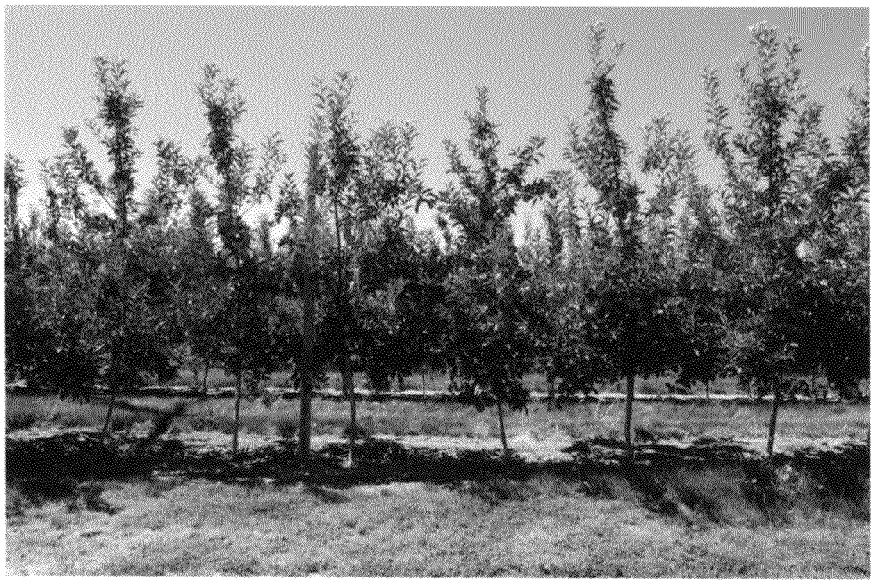

FIG. 1 shows the blossoms of the 'Foxtrot' apple tree;
FIG. 2 shows a 'Foxtrot' apple tree in bloom;
FIG. 3 shows the leaves of the 'Foxtrot' apple tree;
FIG. 4 shows fruit of the 'Foxtrot' apple tree;
FIGS. 5 and 6 show sectioned fruit of the 'Foxtrot' apple tree;
FIG. 7 shows the fruit and leaves of the 'Foxtrot' apple tree;
FIG. 8 shows a 'Foxtrot' apple tree;
FIG. 9 shows a 'Tenroy Gala' apple (left) and a 'Foxtrot' apple (right); and FIG. 10 shows trees of the 'Tenroy Gala' variety (left) and the 'Foxtrot' variety (right).

DETAILED BOTANICAL DESCRIPTION OF THE VARIETY

The following-detailed botanical description is based primarily on observations made during the 2012 growing season near Connell, Wash. The observed trees were planted in 2009 and grown on 'M26' rootstock (not patented) in trellised high-density plantings. All colors are described according to The Royal Horticultural Society Colour Chart. It should be understood that the characteristics described will vary somewhat depending upon cultural practices and climatic conditions, and will vary with location and season. Quantified measurements are expressed as an average of measurements taken from a number of individual plants of the new variety. The measurements of any individual plant or any group of plants of the new variety may vary from the stated average.

Tree:
- *Vigor*.—Moderate (similar to 'Tenroy Gala').
- *Type*.—Spur-type.
- *Habit*.—Upright.
- *Height*.—3.3 m.
- *Trunk diameter* (*at* 30 *cm above the graft*).—5 cm.
- *Bark texture*.—Smooth with prominent lenticels.
- *Bark coloration*.—Grey-brown N200C, N200D, with areas of Grey-brown 199B.

Branch (fruiting branches located at around 1 m above the graft union):
- *Length*.—30 to 60 cm.
- *Diameter*.—2 to 3 cm.
- *Crotch angle*.—45 degrees to 90 degrees.
- *Bark color*.—Greyed-brown N200C, N200D.

One year old shoot:
- *Length*.—30 cm.
- *Color*.—Grey-brown 197B; Grey-brown 200D.
- *Pubescence*.—Moderate (same as 'Tenroy Gala').
- *Thickness*.—5 to 6 mm.
- *Internode length*.—3 to 5 cm.
- *Number of lenticels*.—4 to 6 per $cm^2$.

Flower buds:
*Quantity per spur.*—5.
*Shape.*—Pointed.
*Length.*—5 mm.
*Diameter.*—5 mm.
*Color* (*at time of bud burst, prior to opening*).—Red-purple N57.

Flowers:
*Diameter of fully open flower.*—6 cm.
*Relative position of petal margins.*—Touching.
*Number per cluster.*—5.
*Date of first bloom* (2013).—April 18.
*Date of full bloom* (2013).—April 23.
*Pollinator.*—Required.

Petals:
*Number per flower.*—5 to 6.
*Shape.*—Orbicular.
*Length.*—3 cm.
*Width.*—1.5 cm.
*Apex.*—Obtuse.
*Base.*—Aequilateral.
*Margin.*—Entire, cupped.
*Color of upper surface.*—White to pale pink, with tinges of Red-purple N66C.
*Color of lower surface.*—White to pale pink, with tinges of Red-purple N66C.

Pistils:
*Stigma.*—Yellow 11C.
*Style.*—Yellow-green 145D.
*Ovary.*—Yellow-green 145D.

Stamen:
*Quantity.*—18 to 20.
*Anther.*—Yellow 11D.
*Filament.*—White NN155C.

Pedicel:
*Color.*—Yellow-green 144D.

Sepals:
*Quantity.*—5.
*Shape.*—Pointed.
*Margin.*—Entire.
*Color.*—Yellow-green 145A, pubescent.

Leaves:
*Shape.*—Ovate.
*Length.*—11 cm.
*Width.*—6 cm.
*Blade margin.*—Serrate.
*Apex.*—Acuminate.
*Base shape.*—Aequilateral, oblique.
*Color of upper surface.*—Yellow-green 144A, Green N137A.
*Color of lower surface.*—Yellow-green 147B, 147C.
*Attitude in relation to shoot.*—Upward.

Petiole:
*Length.*—3 to 3.5 cm.
*Diameter.*—2 to 3 mm.
*Color.*—Yellow-green 144D with some anthocyanin coloration.

Fruit:
*Quantity per cluster.*—One.
*Diameter.*—8 cm.
*Weight.*—225 g.
*Ratio of height to width.*—Equal.
*General shape in profile.*—Conic.
*Position of maximum diameter.*—Equator.
*Ribbing.*—Absent.
*Crowning at calyx end.*—Present.
*Size of eye.*—1 cm.
*Aperture of eye.*—Closed.
*Length of sepal.*—6 mm.
*Bloom of skin.*—Absent or weak.
*Greasiness of skin.*—Absent or weak.
*Background color of skin.*—Yellow 7D.
*Amount of over color.*—90 to 100%.
*Over color of skin.*—Red 45A, 44B.
*Intensity of over color.*—Strong to very strong.
*Pattern of over color.*—Solid flush with weakly defined stripes.
*Amount of russet around stalk cavity.*—None.
*Amount of russet on cheeks.*—None.
*Area of russet around eye basin.*—None.
*Length of stalk.*—3 cm.
*Thickness of stalk.*—3 mm.
*Depth of stalk cavity.*—2 cm.
*Width of stalk cavity.*—3.5 cm.
*Depth of eye basin.*—1.3 cm.
*Width of eye basin.*—3 cm.
*Firmness of flesh.*—21 lbs. (at 5 days before harvest).
*Flesh texture.*—Crisp, fine.
*Aroma.*—Fragrant, floral.
*Juiciness.*—Juicy, similar to 'Tenroy Gala'.
*Brix.*—12 (at 5 days before harvest).
*Flesh color.*—Green-white 157D.
*Stem color.*—Grey-brown N199D.

Seeds:
*Quantity per fruit.*—4 to 7.
*Shape.*—Teardrop shape.
*Coloration.*—Grey-brown N199B, N199C.

Harvest:
*Time for harvest.*—Late August, about 5 days prior to 'Tenroy Gala'.
*Number of picks.*—One.
*Harvest yield.*—35 tons per acre (based on high-density planting of 1100 trees per acre).

Disease resistance/susceptibility: None noted.

Market use: Fresh.

The invention claimed is:

1. I claim a new and distinct apple tree substantially as described and illustrated herein.

* * * * *